US008518081B2

(12) United States Patent
Patel et al.

(10) Patent No.: US 8,518,081 B2
(45) Date of Patent: Aug. 27, 2013

(54) LAMINOPLASTY APPARATUS AND METHODS

(76) Inventors: Chetan Patel, Longwood, FL (US); Eeric Truumees, Austin, TX (US); Henry Brown, Ann Arbor, MI (US)

(*) Notice: Subject to any disclaimer, the term of this patent is extended or adjusted under 35 U.S.C. 154(b) by 612 days.

(21) Appl. No.: 12/355,230

(22) Filed: Jan. 16, 2009

(65) Prior Publication Data

US 2010/0185239 A1     Jul. 22, 2010

(51) Int. Cl.
*A61B 17/70* (2006.01)
(52) U.S. Cl.
USPC .............. 606/246; 606/264; 606/279
(58) Field of Classification Search
USPC ................. 606/246–279, 300–321
See application file for complete search history.

(56) References Cited

U.S. PATENT DOCUMENTS

| | | | |
|---|---|---|---|
| 6,080,157 A | 6/2000 | Cathro et al. | |
| 2003/0045935 A1 | 3/2003 | Angelucci et al. | |
| 2003/0125738 A1 | 7/2003 | Khanna | |
| 2003/0125740 A1* | 7/2003 | Khanna | 606/61 |
| 2005/0107877 A1 | 5/2005 | Blain | |
| 2005/0149030 A1* | 7/2005 | Serhan et al. | 606/73 |
| 2006/0058790 A1* | 3/2006 | Carl et al. | 606/61 |
| 2008/0009865 A1* | 1/2008 | Taylor | 606/61 |
| 2008/0215096 A1 | 9/2008 | Nash et al. | |
| 2009/0312798 A1* | 12/2009 | Varela | 606/247 |

OTHER PUBLICATIONS

Mountaineer OCT Spinal System Product Catalog, DePuy Spine, 2005.
Mountaineer OCT Spinal System Surgical Technique, DePuy Spine, 2005.

* cited by examiner

*Primary Examiner* — Eduardo C Robert
*Assistant Examiner* — Christina Negrellirodriguez
(74) *Attorney, Agent, or Firm* — Gifford, Krass, Sprinkle, Anderson & Citkowski, P.C.

(57) ABSTRACT

A simple yet effective adjustable laminoplasty implant and procedure includes a member positioned within or through a hole formed through a spinous process, and an elongated element is provided with a medial end coupled to the member and a lateral end configured for engagement with a bone mass fixation device. The elongated element may be a bent rod. The rod may have a medial end with a cross-section that is smaller than that of the lateral end. The member positioned within or through a hole formed through a spinous process may be a sleeve with angled endcaps. The endcaps may include bone-engaging teeth. Alternatively, the sleeve may have a central bore and barbs that engage with surrounding bone when an elongated member is inserted in the bore. The mass fixation device may a pedicle screw. The pedicle screw may be configured to receive a transverse rod. Alternatively, the mass fixation device may itself be a rod. Method of performing a laminoplasty In accordance with the invention are also disclosed.

10 Claims, 7 Drawing Sheets

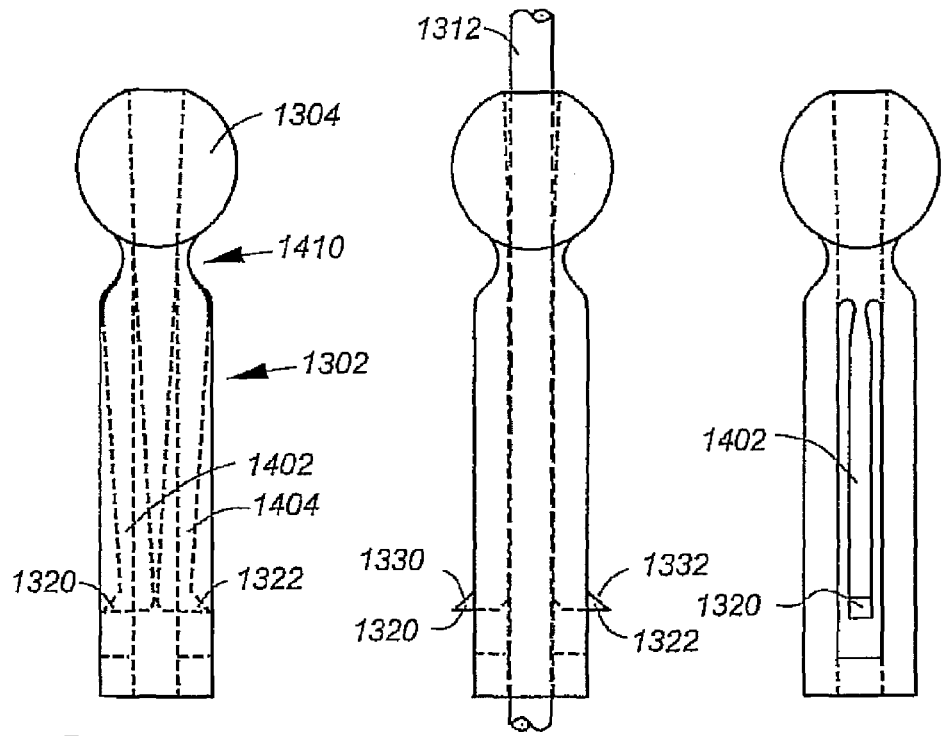
Fig - 13A  Fig - 13B  Fig - 13C
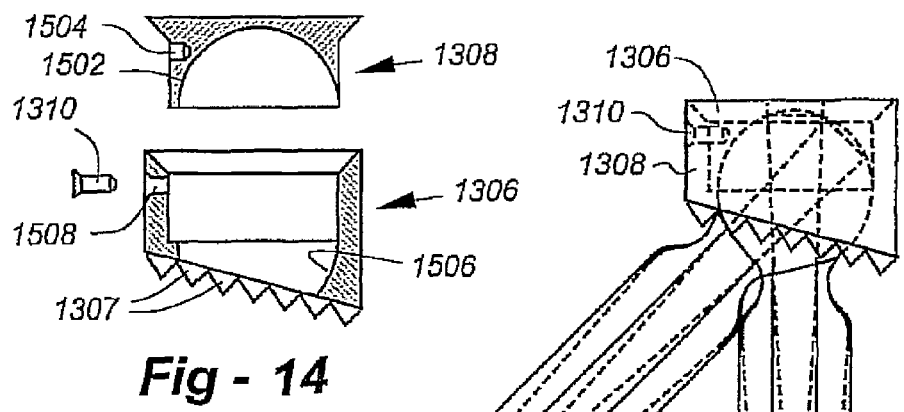
Fig - 14
Fig - 15

LAMINOPLASTY APPARATUS AND METHODS

BACKGROUND OF THE INVENTION

This invention relates generally to laminoplasty and, in particular, to a simple yet effective adjustable implant and procedure.

BACKGROUND OF THE INVENTION

Laminoplasty is a surgical procedure for treating spinal stenosis by relieving pressure on the spinal cord. The procedure involves the cutting (cutting through on one side and merely cutting a groove on the other) the lamina on both sides of the affected vertebrae and then "swinging" the freed flap of bone open thus relieving the pressure on the spinal cord. The spinous process may be removed to allow the lamina bone flap to be swung open. The bone flap is then propped open using small wedges or pieces of bone such that the enlarged spinal canal will remain in place.

Often a small metal plate is used to bridge the open gap and help the bone graft remain in place. Laminoplasty systems on the market today use simple bone plates for fixation and, due to the small area being plated, require extremely small plates. These are often difficult to place and use very small screws that can be lost of difficult to manipulate.

SUMMARY OF THE INVENTION

This invention resides a simple yet effective adjustable laminoplasty implant and procedure. Broadly, a member is positioned within or through a hole formed through a spinous process, and an elongated element is provided with a medial end coupled to the member and a lateral end configured for engagement with a bone mass fixation device.

In one embodiment, the elongated element is a bent rod. The rod may have a medial end with a cross-section that is smaller than that of the lateral end. The member positioned within or through a hole fanned through a spinous process may be a sleeve with angled endcaps. The endcaps may include bone-engaging teeth. Alternatively, the sleeve may have a central bore and barbs that engage with surrounding bone when an elongated member is inserted in the bore. The mass fixation device may a pedicle screw. The pedicle screw may be configured to receive a transverse rod. Alternatively, the mass fixation device may itself be a rod.

A method of performing a laminoplasty according to the invention comprises the steps of:
  forming a hole through a spinous process;
  positioning a member in the hole;
  resecting a lamina and moving the spinous process to form a gap in the lamina;
  coupling the member to bone mass on a vertebral body.

The method may further include the step of positioning bone graft material in the gap.

BRIEF DESCRIPTION OF THE DRAWINGS

FIG. 13A is a detail drawing of a sleeve and expandable arms;
FIG. 13B is a detail drawing showing how, when the rod is inserted, the arms are pushed apart, enabling tips to engage with surrounding bone;
FIG. 13C is a detail drawing from a different perspective showing one arm with associated tip;
FIG. 14 is a detail drawing in partial cross section showing a toothed washer and topcap washer;
and
FIG. 15 shows how the assembly of FIGS. 12-14 allows for polyaxial orientation of the sleeve at angles up to 45 degrees and greater.

DETAILED DESCRIPTION OF THE INVENTION

Figure 1:
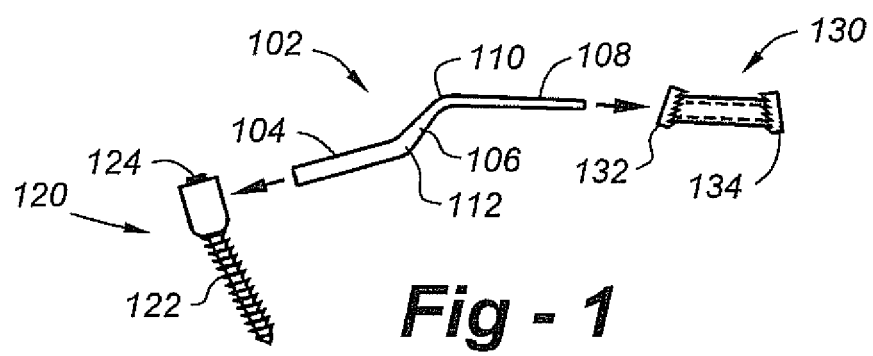
FIG. 1 is a laminoplasty implant according to the invention that includes a bent rod, fixation screw and sleeve.

This invention improves upon laminoplasty devices and methods by providing a simple yet effective adjustable implant and procedure. One implant according to the invention, shown in FIG. 1, includes bent rod 1027, fixation screw 120, and sleeve 130. Rod 102 has a lateral end 104, midsection 106 and medial end 108. The diameter of the rod preferably necks down from a larger-diameter lateral end to a smaller-diameter medial end. The cross section of the rod is preferably circular throughout though non-round geometries may alternatively be used to resist rotation in certain directions, for example.

In this embodiment, rod 102 preferably includes two bends 110, 112 thereby forming right or obtuse angles between midsection 106 and ends 104, 108. The bends may be in the same plane or not depending upon patient physiology. Rod 102 may be provided with a predetermined shape and/or manipulated by the surgeon during the implantation procedure.

Sleeve 130 has an inner diameter slightly less that the outer diameter of the medial end 108 of rod 102. The sleeve has endcaps 132, 134, at least one of which is press-fit onto the sleeve after installation as described in more detail subsequently. In the preferred embodiment, the endcaps 132, 134 are angled relative to the axis of the sleeve and include bone-engaging teeth as shown.

Fixation screw 120 may be any type of fastener having bone-engaging threads 122, including commercially available monoaxial or polyaxial pedicle or lateral-mass screws such as those used in the DePuy Spine Mountineer or MDT Vertex systems. During implantation, lateral end 104 of rod 102 is inserted into the body portion of the fastener and tightened, typically with a set screw 124. The invention need not include fastener 120 is such a fastener is already provided, for example, as part of a plate or rod system.

Figure 2:
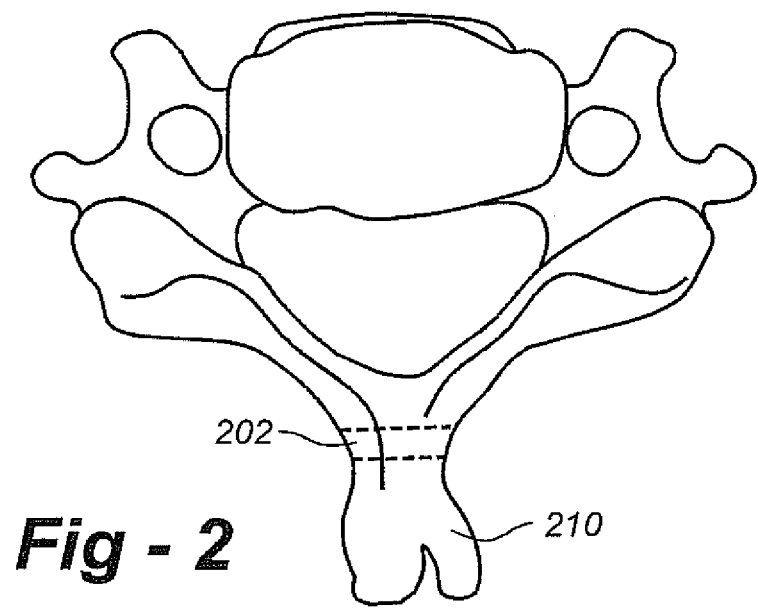
FIG. 2 shows a hole formed through a spinous process of a cervical vertebral body.
Figure 3:
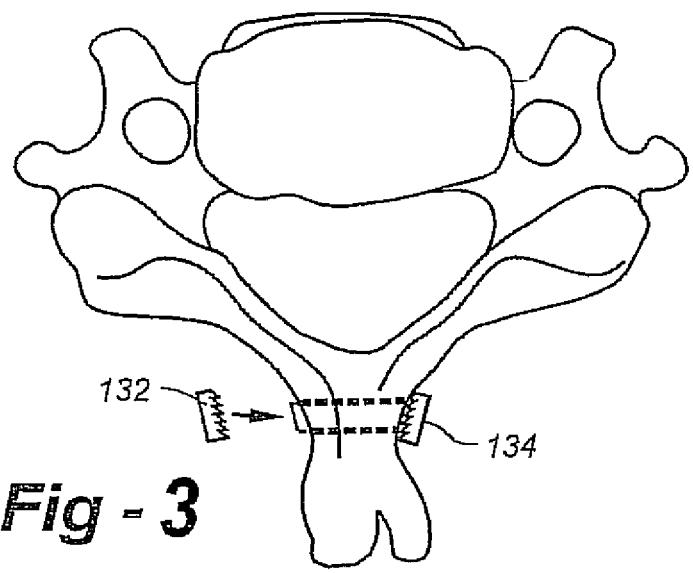
FIG. 3 illustrates the attachment of an endcap.

FIGS. 2-8 depict the implantation procedure from a top-down perspective. In FIG. 2, a hole 202 has been formed through spinous process 210 of a cervical vertebral body. While a drill may be used, hole 202 is preferably formed with a punch much like a leather punch. While this hole may be formed later in the procedure, it is preferably carried out before laminar resection. The intended entry point is at the base of the spinous process; i.e., at the junction with the lamina.

Figure 4:
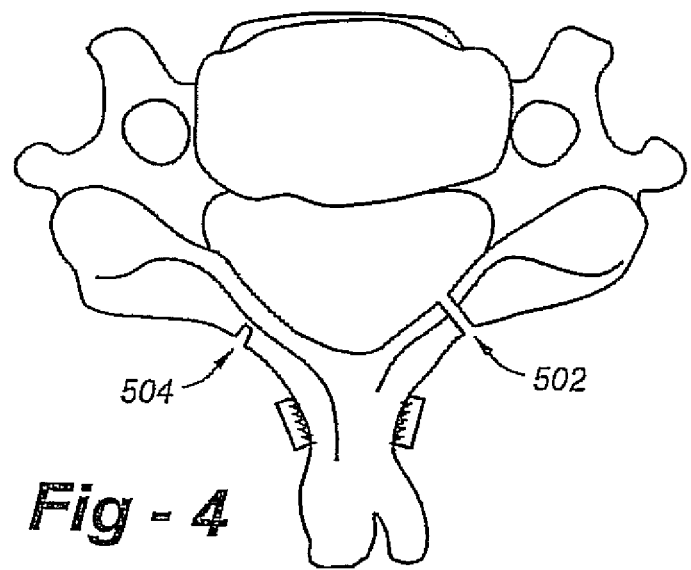
FIG. 4 shows one resected lamina and a weakening groove formed into the other lamina in accordance with standard laminoplasty procedures.
Figure 5:
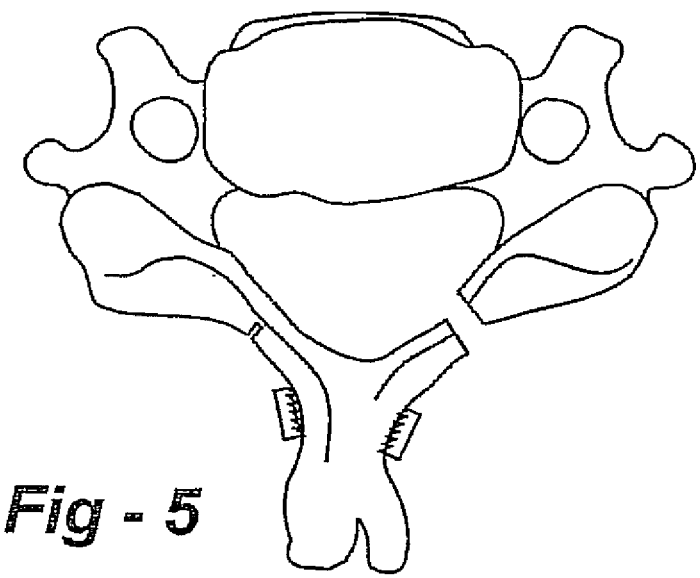
FIG. 5 depicts the spinous process being bent outwardly to a desired degree.

In FIG. 4, one lamina is resected at 502 and a weakening groove 504 is formed into the other lamina in accordance with standard laminoplasty procedures. The spinous process is then bent outwardly to a desired degree as shown in FIG. 5.

Figure 6:
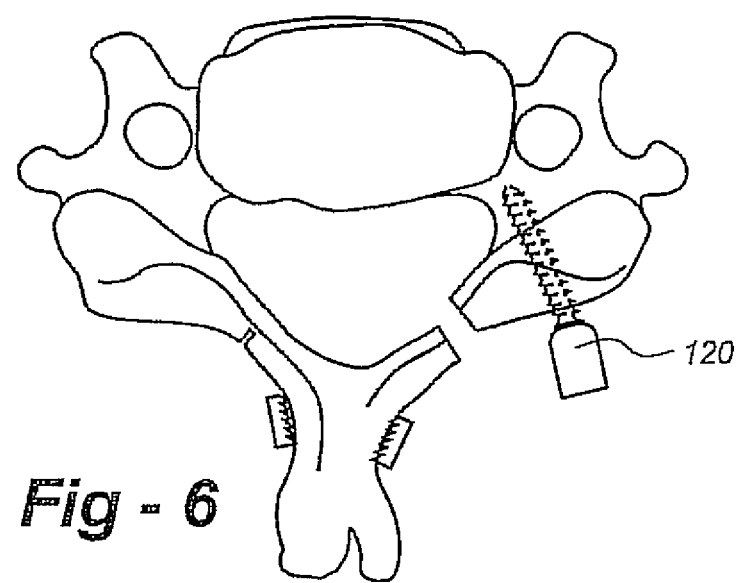
FIG. 6 shows a polyaxial screw being installed.
Figure 7:
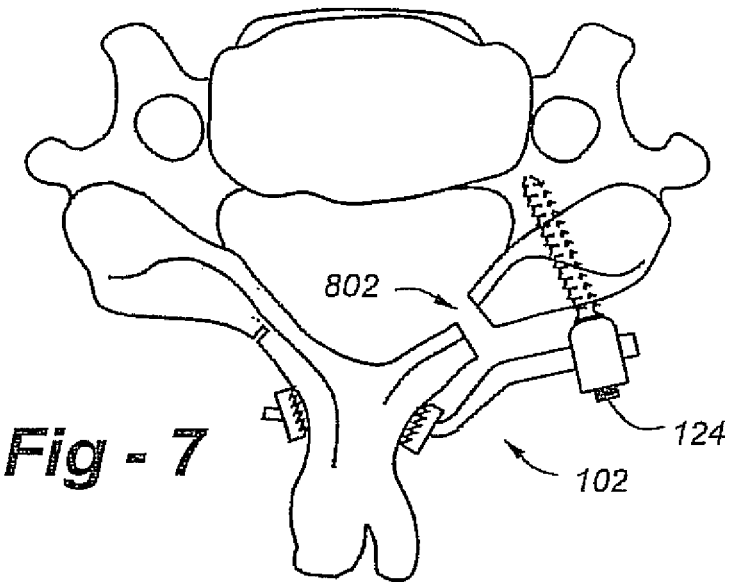
FIG. 7 illustrates an installed rod being tightened into position with a set screw.

In FIG. 6, a polyaxial screw 120 has been installed, and in FIG. 7, rod 102 has been installed and tightened into position with set screw 124. Note that rod 102 is loosely inserted into sleeve 130, providing for a somewhat dynamic coupling, such that the bone interface is not subject to constant stress, which could lead to the "window wiper" effect in bone.

Figure 8:
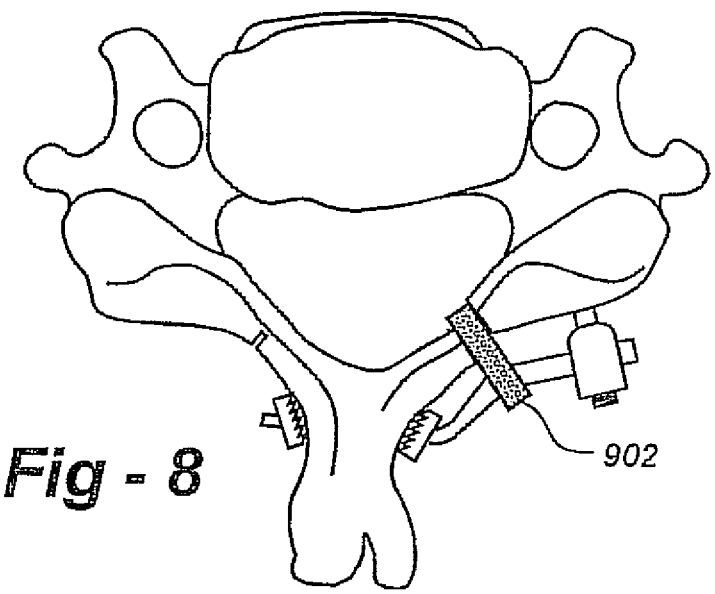
FIG. 8 shows a piece of machined bone graft with a groove or hole enabling engagement with the rod.

Bone graft may be added in the opened laminar gap 802 in several ways. For example, a piece of machined bone graft may be provided with a groove or hole enabling piece 902 to engage with rod 102 as shown in FIG. 8. Alternatively, a hole may be provided in rod 102 enabling separate fastener to hold a piece of bone graft in a desired position.

Figure 9:
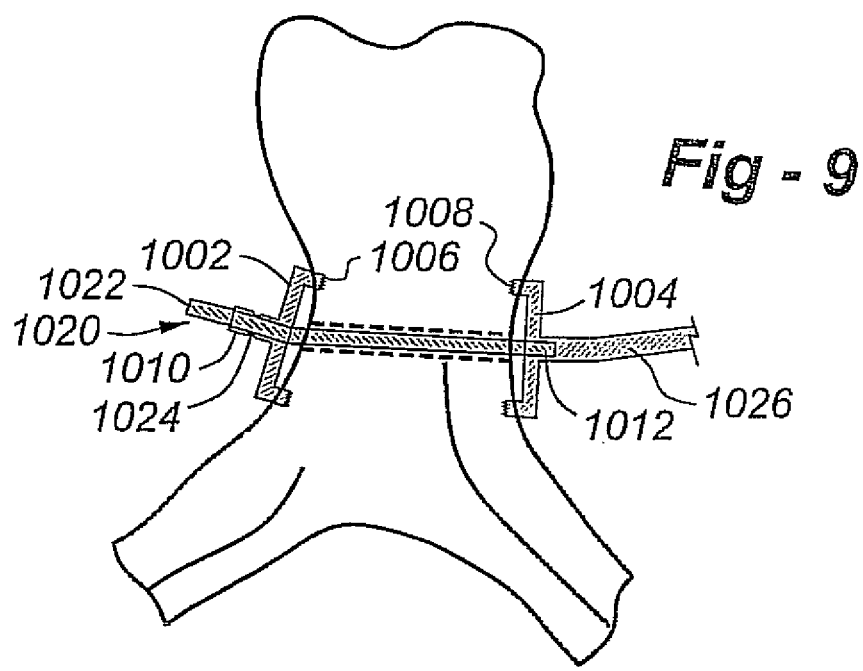
FIG. 9 illustrates the use of flexible element made of braided stainless steel of other appropriate material.

Although the embodiments described thus far have used a rigid, bend rod as the sole interconnect device, other or additional elongate elements may alternatively be used. FIG. 9, for example, illustrates the use of flexible element 1020 made of braided stainless steel of other appropriate material. In the embodiment shown, element 1020 has a first end 1012 welded or otherwise attached to end cap 1004 and another end 1022 threaded though end cap 1002 and held in position with a crimp 1024 in collar 1010. Cap 1004 forms parts of rod 1026 which extends to some form of bone-mass fixation device (not shown). Both of the caps 1002, 1004 each preferably include bone-engaging teeth 1006, 1008. The use of a flexible element with crimping may allow both collars to better conform to the angles and contours of the spinous process.

Figures 10, 11:
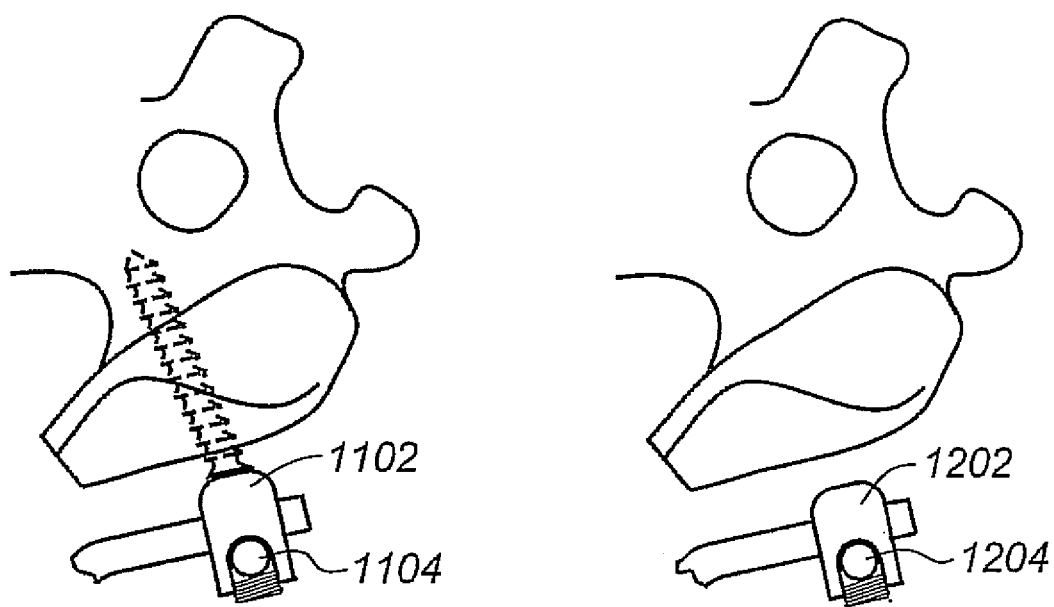
FIG. 10 shows how a fixation screw may include a body 1102 with a slot to accept a transverse fixation rod.
FIG. 11 shows how a threaded screw may be eliminated at a particular level, with fixation relying instead on a body coupled only to transverse rod.

Different types of bone-mass fixation devices may also be used. For example, fixation screw 120 introduced in FIG. 1 may include a body 1102 with a slot to accept a transverse fixation rod 1104, as shown in FIG. 10. Indeed, depending upon available instrumentation, the threaded screw may be eliminated at a particular level, with fixation relying instead on a body 1202 couple only to transverse rod 1204 as depicted in FIG. 11.

Figure 12A:
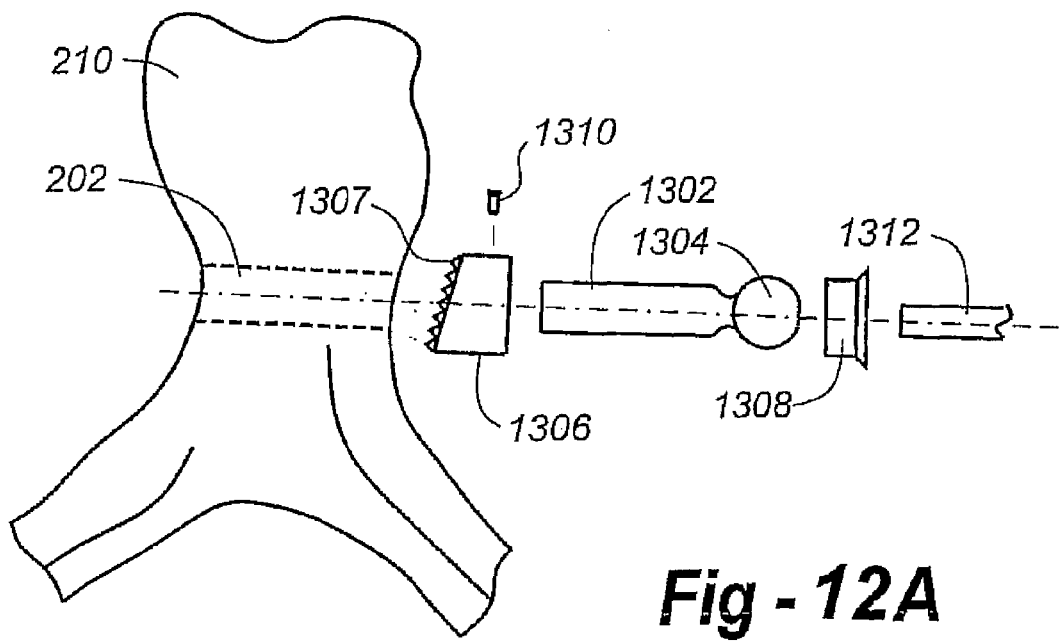
FIG. 12A begins a sequence of drawings that illustrate an alternative fixation apparatus that requires access to only one side of the spinous process.
Figure 12B:
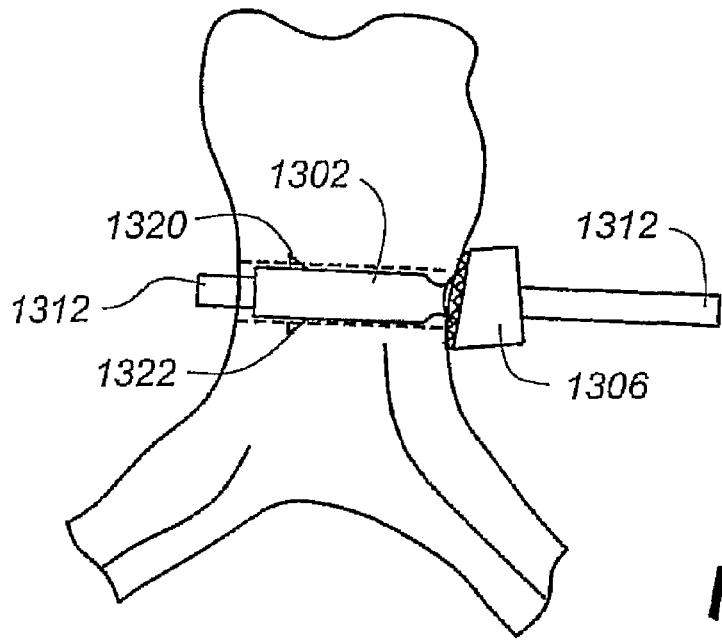
FIG. 12B depicts a sleeve with a central bore and expanding arms, each with bone-engaging barbs, such that when a rod is pushed into the central bone the arms are pushed apart, causing the barbs to engage.

FIG. 12A begins a sequence of drawings that illustrate an alternative fixation apparatus that requires access to only one side of the spinous process 210. This embodiment includes a sleeve 1302 having a spherical head 1304. The sleeve is journaled through a toothed washer 1306 which retains a portion of the head 1304. A topcap washer 1308, inserted into a proximal opening in toothed washer 1306 and assembled with pin 1310, fully retains the head 1304 in polyaxial fashion. The sleeve has a central bore with expanding arms 1402, 1404, each with bone-engaging barbs 1320, 1322, better seen in FIGS. 13A-C. When a rod 1312 is pushed into the central bone, as shown in FIG. 12B, the arms 1402, 1404 are pushed apart, causing the barbs 1320, 1322 to engage.

FIG. 13A is a detail drawing of the sleeve 1302, showing arms 1402, 1404. FIG. 13B is a detail drawing showing how, when rod 1312 is inserted, the arms are pushed apart, enabling tips 1320, 1322 to engage with surrounding bone. FIG. 13C is a detail drawing from a different perspective showing one arm 1402 with tip 1320. Note that, by virtue of ramps 1330, 1332 on barbs 1320, 1322, the biting motion of the barbs will pull the sleeve slightly toward the spinous process, further securing the sleeve in the bone. Also, necked-down portion 1410 minimizes the overall size of the assembly while maximizing swivel range as shown in FIG. 15.

FIG. 14 is a detail drawing in partial cross section showing the toothed washer 1306 and topcap 1308. As mentioned, toothed washer 1306 includes one concave articulating surface 1506 that cooperates with a portion of head 1304, while topcap 1308 includes an additional concave surface 1502 that also cooperates with head 1304 on sleeve 1302. When assembled, as shown in FIG. 15, this allows for polyaxial orientation of the sleeve from 1302 position 1302a to 1302b at angles up to 45 degrees and greater.

The various components associated with this invention, including sleeve 1302 and washers 1306, 1308, may be made from any biocompatible materials such as titanium, chrome-cobalt or other metals, ceramics, certain plastics and composites.

We claim:

1. Laminoplasty apparatus, comprising:
    a sleeve with a central bore therethrough adapted to be positioned within and through a hole formed through a spinous process having opposing outer surfaces and forming part of a vertebral body, the sleeve being positioned such that each end of the sleeve coincides with one of the outer surfaces of the spinous process;
    a bone mass fixation device adapted to be implanted into the vertebral body; and
    a bent rod having a medial end configured for insertion into the central bore of the sleeve and a lateral end configured for engagement with the bone mass fixation device.

2. The laminoplasty apparatus of claim 1, wherein:
    the elongated element is a bent rod; and
    the medial end has a smaller cross-section that the lateral end.

3. The laminoplasty apparatus of claim 1, wherein the sleeve includes endcaps at different angles adapted to engage with the respective outer surfaces of the spinous process.

4. The laminoplasty apparatus of claim 1, wherein the sleeve includes endcaps at different angles with bone-engaging teeth adapted to engage with the respective outer surfaces of the spinous process.

5. The laminoplasty apparatus of claim 1, wherein:
    the hole formed through a spinous process has an inner wall; and
    the sleeve includes barbs that engage with the inner wall when the elongated member is inserted in the bore.

6. The laminoplasty apparatus of claim 1, wherein the mass fixation device is a pedicle screw.

7. The laminoplasty apparatus of claim 1, wherein the mass fixation device is a pedicle screw configured to receive a transverse rod in addition to the bent rod.

8. The laminoplasty apparatus of claim 1, wherein the mass fixation device is a rod.

9. A method of performing a laminoplasty, comprising the steps of:
    forming a hole entirely through a spinous process;
    positioning a member in the formed hole;
    resecting a lamina and moving the spinous process to form a gap in the lamina;
    coupling the member to bone mass on a vertebral body.

10. The method of claim 9, further including the step of positioning bone graft material in the gap.

* * * * *